United States Patent [19]
Vogelstein et al.

[11] Patent Number: 6,054,570
[45] Date of Patent: *Apr. 25, 2000

[54] SELECTIVE EXPRESSION OF DESIRED GENES IN CELLS EXPRESSING ONCOPROTEINS

[75] Inventors: Bert Vogelstein, Baltimore; Kenneth W. Kinzler, BelAir; Luis da Costa, Columbia; Jin Jen, Baltimore, all of Md.

[73] Assignee: The Johns Hopkins University, Baltimore, Md.

[ * ] Notice: This patent is subject to a terminal disclaimer.

[21] Appl. No.: 09/163,563

[22] Filed: Sep. 30, 1998

Related U.S. Application Data

[63] Continuation of application No. 08/620,341, Mar. 22, 1996.
[51] Int. Cl.⁷ .................................................. C07H 21/04
[52] U.S. Cl. ...................... 536/23.4; 536/23.1; 536/23.5; 536/24.1
[58] Field of Search ............................ 935/6, 7.1, 320.1, 935/440, 455; 536/23.1, 28.4, 23.5, 24.1

[56] References Cited

U.S. PATENT DOCUMENTS 5,866,340  2/1999  Vogelstein et al. ...................... 435/7.1

OTHER PUBLICATIONS

Moolten, F.L.Karp et al. An Alternative to the Magic Bullet Paradigm for Specific Cancer Therapy. Medical Hypothesis. 1987. vol. 24, pp. 43–51.
Karp et al. Nature Medicine 1:309–320 (1995).
Fields et al. Trends Genet. 10:286–292 (1994).
Gyuris et al.,Cell 75:791–803 (1993).
Germino et al., Proc. Natl. Acad. Sci. USA 90:933–937 (1993).
Hurford, R.K. et al., Gene Therapy of Metastatic Cancer by in vivo Retroviral Gene Targeting. Nature Genetics. Aug. 1995, vol. 10, pp. 430–435.
Verma et al. Nature, Sep. 18, 1997, vol. 389, pp. 239–242.
Barinaga, M. Science, vol. 266, p. 1326.
Marshall, E. Science, vol. 269, pp. 1050–1055.
Crystal, R.G. Sicence, vol. 270, pp. 404–410.
Orkin et al. Report and Recommendations of the Panel to Assess the NIH Investment in Research on Gene Therapy.
Jolly, D. Cancer Gene Tehrapy, vol. 1 (1)pp. 51–64.
Marshall, E.M. Science. vol. 269, pp. 1050–1055, Aug. 1995.
Crystal, R.G. Science. vol. 270, pp. 404–410, 1995.
Jolly, D. Cancer Gene Therapy, vol. 1(1), pp. 51–64, 1994.
Verma et al. Nature. vol. 389, pp. 239–242, Sep. 1997.
Nature Biotechnology, editorial. vol. 15, Sep. 1997.
Jarnoff, L. Time. vol. 153(1), pp. 68–73, Jan. 1999.

*Primary Examiner*—Remy Yucel
*Attorney, Agent, or Firm*—Banner & Witcoff, Ltd.

[57] ABSTRACT

Over the past decade, it has become clear that tumorigenesis is driven by alterations in genes that control cell growth or cell death. Theoretically, the proteins encoded by these genes provide excellent tools for achieving tumor cell-specific expression. An approach to achieving specific expression of a desired protein in tumor cells is based on the selective expression of such oncoproteins. In outline, an endogenous cellular oncoprotein binds to exogenously introduced gene products, resulting in transcriptional activation of a desired gene. This approach is generally applicable to other diseases in which a particular protein is selectively expressed in disease-affected cells as compared to non-affected cells.

5 Claims, 8 Drawing Sheets

SELECTIVE EXPRESSION OF DESIRED GENES IN CELLS EXPRESSING ONCOPROTEINS

This application is a continuation of Ser. No. 08/620,341 filed Mar. 22, 1996.

This invention was made using funds from the U.S. National Institutes of Health, grants CA35494 and CA43460. The U.S. government therefore retains certain rights in the invention.

TECHNICAL FIELD OF THE INVENTION

The present invention relates to DNA constructs for selectively expressing proteins in tumor cells, virally infected cells, and other diseased cells. Such constructs can be used diagnostically or therapeutically.

BACKGROUND OF THE INVENTION

The success of a diagnostic or therapeutic strategy is critically dependent on its specificity. Therapies for infectious diseases achieve high specificity because they target metabolic pathways that differ between the pathogen and the host. The applicability of this concept to cancer, however, has been limited by the difficulty in defining metabolic features that are specific to tumor cells. As a result, current cancer therapeutic agents have largely been found through empiric screening programs rather than through rational design.

Knowledge of the genetic alterations that drive neoplasia has revolutionized cancer research over the past two decades (Stillman, 1994). Theoretically, this knowledge provides a large number of potential diagnostic and therapeutic targets in the form of mutant oncoproteins in the resultant tumors. In general, however, it has not been clear how to use such knowledge to design new diagnostic and therapeutic strategies (Karp, 1995). Thus, there is a need in the art for new diagnostic and therapeutic strategies for combatting cancers.

SUMMARY OF THE INVENTION

It is an object of the invention to provide genetic constructs for use in diseased cells, such as tumor cells and virally infected cells.

It is an object of the invention to provide fusion proteins for regulating expression of desired proteins in diseased cells, such as tumor cells and virally infected cells.

It is another object of the invention to provide methods of selectively expressing proteins in diseased cells, such as tumor cells and virally infected cells.

It is yet another object of the invention to provide methods of detecting cells which selectively express a protein.

These and other objects of the invention are provided by one or more of the embodiments described below. In one embodiment of the invention a set of genetic constructs is provided. The set comprises a weapon construct and a trigger construct. The weapon construct comprises a gene coding sequence of a desired protein, and an inducible upstream activating sequence which is upstream of the gene coding sequence, wherein the gene coding sequence is inducible by a transcription factor which binds to the upstream activating sequence. The trigger construct comprises a nucleotide sequence encoding a first fusion protein comprising a DNA-binding domain which can bind to the upstream activating sequence, and a killer binding domain which binds to a disease marker protein which is selectively expressed in a diseased cell, wherein the first fusion protein does not contain a transactivation domain. Optionally, the set may also comprise a transactivation construct which comprises a nucleotide sequence encoding a second fusion protein comprising a killer binding domain which binds to an oncoprotein, and a transactivation domain which when part of a protein complex which binds to the upstream activating sequence activates expression of the weapon construct.

In another embodiment of the invention, a method for obtaining selective expression of a desired protein in cells which selectively express a disease marker protein is provided. The method comprises the step of introducing into a population of cells a set of genetic constructs, whereby the desired protein is expressed selectively in those cells which express the disease marker protein. The set of genetic constructs are as described above.

In yet another embodiment of the invention, a method is provided to detect cells which express a disease marker protein which is selectively expressed in a diseased cell. The method comprises the steps of introducing into a population of cells a set of genetic constructs, whereby a desired protein is expressed selectively in those cells which express the disease marker protein, and detecting those cells which express the desired protein.

These and other embodiments of the invention provide the art with reagents and methods for identifying disease marker protein-expressing cells, and selectively expressing desired proteins in those cells. These reagents and methods can be used diagnostically, analytically, and therapeutically. The general strategy described here and evaluated in the p53 model system represents a new diagnostic and therapeutic approach. It makes practical use of pathogenically-related genetic alterations found in a wide variety of tumors, and therefore can legitimately be called "rationally designed".

BRIEF DESCRIPTION OF THE DRAWINGS

FIG. 1 shows a general strategy used to convert cancer genes into killer genes. A "weapon", a "trigger", and a transactivation domain (TAD)-containing construct are introduced into cells by gene transfer. The weapon is under control of an upstream activating sequence (UAS) which binds to the trigger through a specific DNA-binding domain (DBD). In normal cells (top), the trigger cannot stimulate transcription of the weapon, while in cancer cells (bottom) an overexpressed oncoprotein (the "killer") interacts with the trigger and TAD through a killer-binding domains (KBD) to form a novel UAS-specific transcription factor. When a TAD is naturally present in the oncoprotein, there is no need to introduce it exogenously. Transcriptional activation of the weapon by the complex results in expression of the "weapon" gene.

FIGS. 2A and 2B illustrate a strategy used to specifically kill cells expressing high levels of mutant p53. (FIG. 2A) Schematic. A novel transcription factor is generated when the trigger interacts with p53 through its p53-binding domain (p53BD). The trigger-p53 heterodimer binds the GAL4 responsive $UAS_G$ sequences in the PNP (purine nucleoside phosphorylase) gene promoter through the trigger's GAL4 DNA binding domain (GAL4BD) and it stimulates expression of PNP via the transactivation domain of p53. PNP catalyses the conversion of the non-toxic pro-drug MeP-dR (6-methylpurine-deoxyriboside) to the toxic MeP (6-methylpurine), leading to cell death. (FIG. 2B) Constructs. $UAS_G$-βGal and $UAS_G$-PNP are reporter and weapon constructs, respectively. They share a GAL4-responsive promoter that include 5 tandem copies of the GAL4 binding site (UAS$_G$). TA and P5 are trigger constructs, each formed by fusion of the GAL4 DNA binding domain (DBD) to a p53 binding domain (p53BD). The p53BD in trigger TA consists of aa 84–708 of the SV40 large T antigen, while that in P5 consists of aa 305–393 of human p53. Trigger gene expression is driven by a promoter/enhancer from SV40. Killer plasmids contain the coding region of human p53 genes under control of a constitutive CMV promoter/enhancer.

FIGS. 3A–3C show trigger evaluation with a reporter construct. Relative β-galactosidase activity in cells transfected with UAS$_G$-βGal reporter and other constructs are presented. (FIG. 3A) Cell line H1299, trigger TA. (FIG. 3B) Cell line H1299, trigger P5. (FIG. 3C) Cell line 293, trigger P5. Bars and brackets represent means and standard deviations, respectively, from triplicate assays, normalized to the activity of the reporter alone.

FIGS. 4A and 4B show selective gene expression and consequential cell killing using a weapon construct. (FIG. 4A) Cells were transfected with the following constructs: Control: pBluescript alone; Killer(−): trigger P5 plus weapon UAS$_G$-PNP; Killer(+): trigger, weapon and killer pCEP4-p53R273H. The number of morphologically intact cells was assessed five days after adding the indicated concentrations of MeP-dR. (FIG. 4B) Following drug treatment, cells were harvested and various dilutions seeded in new flasks, as described in Materials and Methods. The relative number of colonies present at 7–8 days is shown.

DETAILED DESCRIPTION OF THE INVENTION

Figure 1:
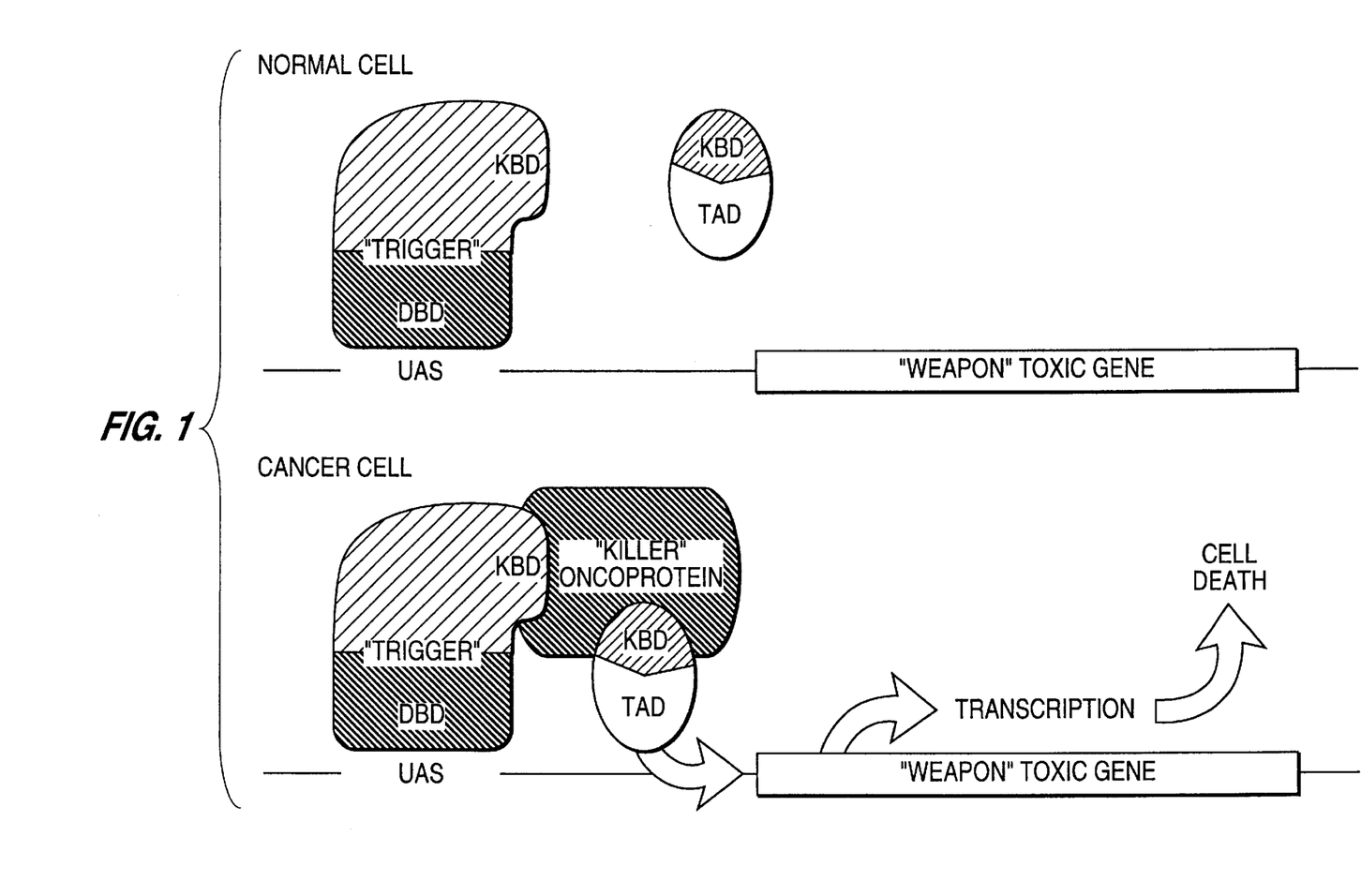

The present inventors have found that genetic alterations integral to disease development can be used to selectively target diseased cells for specific gene expression. As schematically depicted in FIG. 1, an intracellular protein complex is created by binding a disease marker protein (such as an oncoprotein) to exogenously introduced nuclear proteins. The resultant complex then activates expression of a desired gene. Because the rate of complex formation should be directly related to the cellular concentration of the disease marker protein, the strategy can potentially target not only novel oncoprotein, but any protein which is over-expressed as a direct or indirect result of the genetic alterations responsible for disease.

Disease marker proteins can be the products of endogenous cellular genes which are induced during disease. Disease marker proteins can be normal proteins which are overexpressed during disease. Disease marker proteins can be viral genes. Diseases during which proteins are selectively expressed include, but are not limited to cancer, viral diseases, and autoimmune diseases.

Figure 2A:
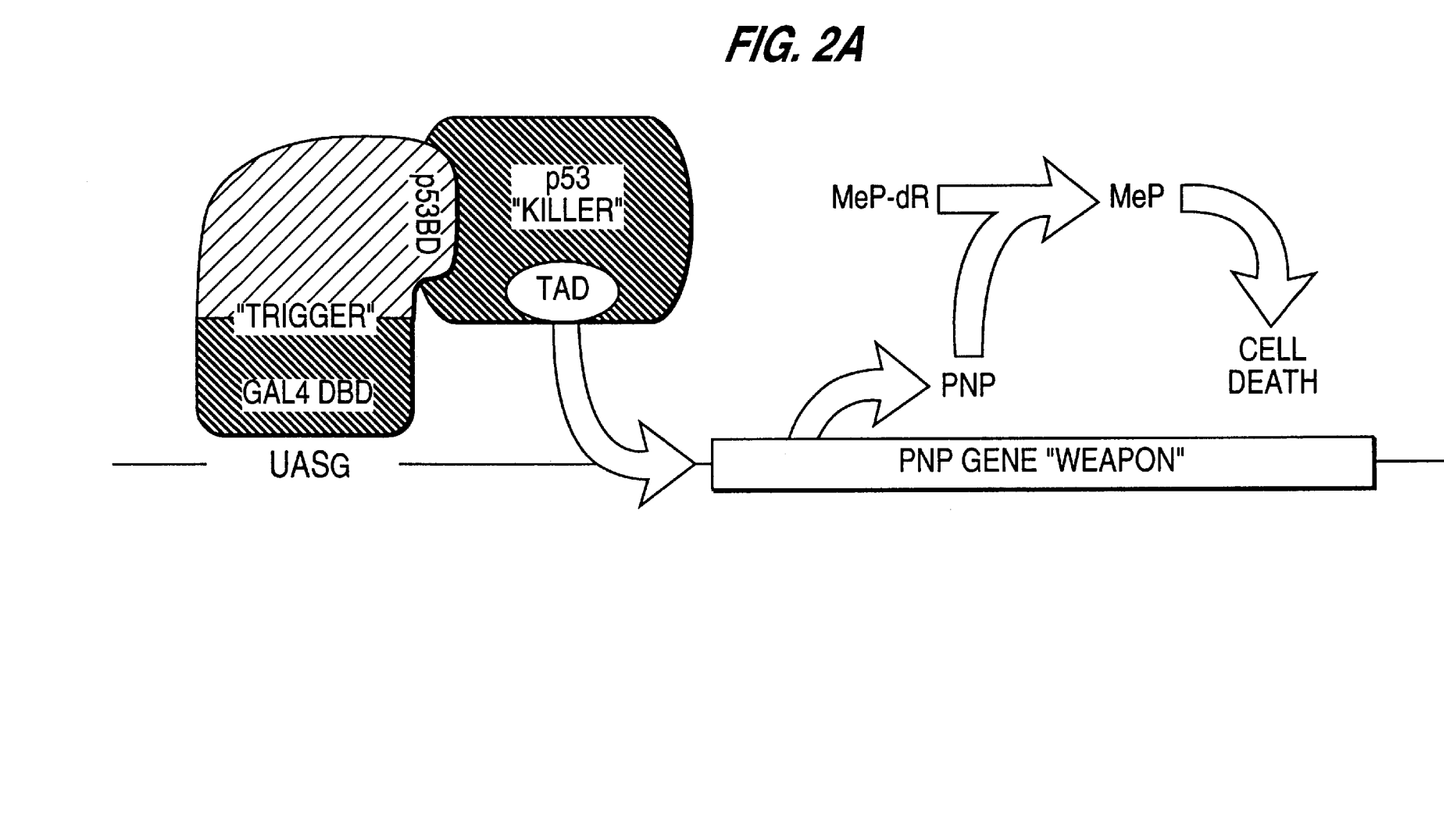
Figure 2B:
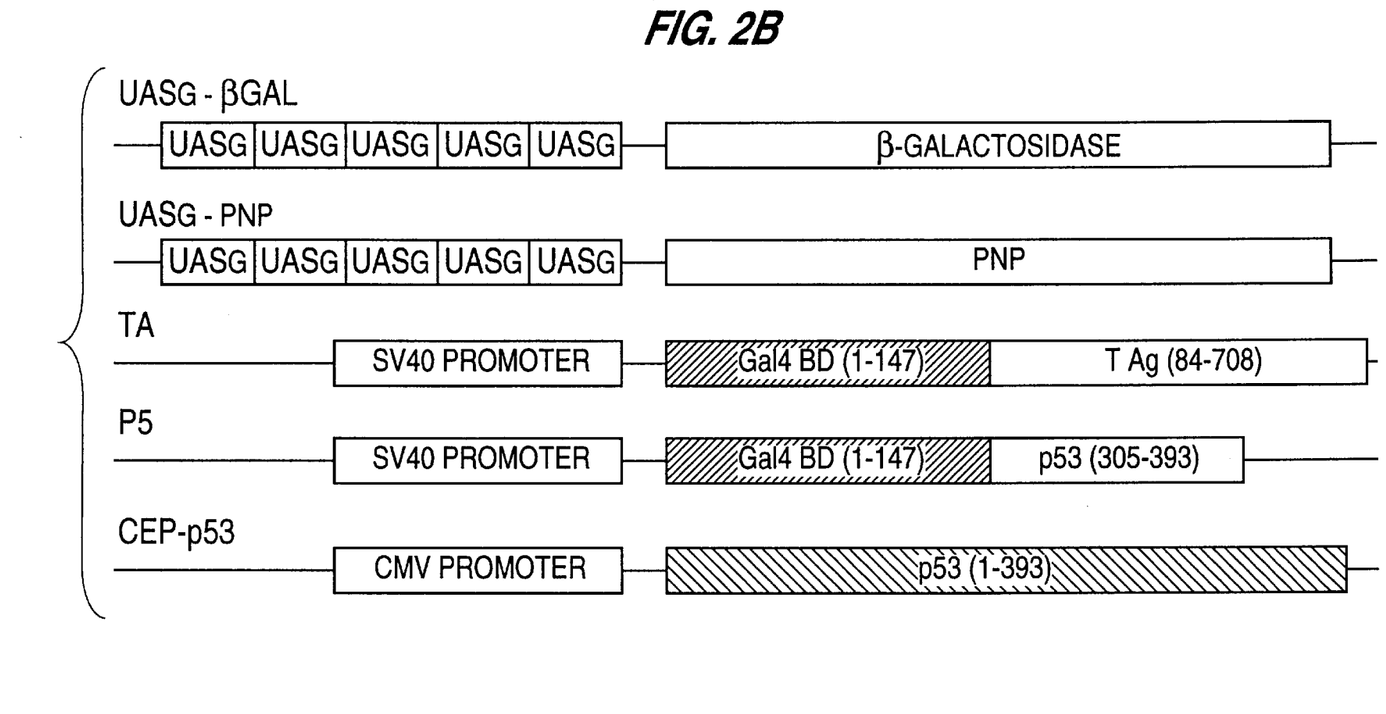

The strategy outlined in FIGS. 1 and 2 results in substantial selective expression for cells over-expressing a mutant oncoprotein relative to cells not expressing the mutant oncoprotein. This strategy is applicable to p53 as well as to other genes involved in neoplasia, such as Rb, ras, neu, myc, erbB2, Bax2, bcl2, APC, MCC, and DCC, as well as to other genes involved in viral and autoimmune diseases. Many oncogenic proteins, like mutant p53, have intrinsic transactivation domains (TAD's), simplifying the approach. Disease marker proteins normally present in the cytoplasm (rather than the nucleus) can also be used. They can be translocated to the nucleus through interaction with triggers containing nuclear localization signals (Finkel, 1993). Powerful techniques for identifying polypeptides that interact with given proteins have been developed in the past few years, (Fields, 1994; Gyuris, 1993; Germino, 1993; Finkel, 1993), facilitating the design of KBD's for trigger and TAD constructs. Novel domains, such as the ones found in foreign (e.g., viral) or mutant proteins represent the most attractive disease marker proteins for use in the present invention, but do not exhaust the possibilities. Any gene which is selectively over-expressed in a tumor cell (e.g., telomerase, cyclins, myc) or other diseased cell represents a potential target. The expression efficacy of the weapon should be directly related to the concentration of the disease marker protein in the diseased cells. Selectivity will be limited by the concentration of the disease marker proteins in non-diseased cells. Selective expression by a diseased cell is preferabley expression of at least 50% more of a marker protein than a non-diseased cell expresses. More preferably, the ratio of expression in a diseased relative to a not-diseased cell is greater than 2, 5, 10, or 50.

A set of genetic constructs, according to the present invention are genetically engineered, recombinant nucleic acids, which are used in a single diagnostic or therapeutic method. Typically they are introduced into the same cells where they, and their gene products can interact. They may be packaged in a kit, in separate containers or mixed. Instructions and ancillary reagents may also be provided. Particularly desirable are reagents for facilitating transfection of cells with the DNA constructs. Such reagents are well known in the art. The constructs may be provided in liquid, frozen, or dehydrated form. The constructs may be on linear or circular molecules; they may be on autonomously replicating molecules or on molecules without replication sequences. At a minimum, the set comprises two constructs, a weapon and a trigger. Optionally, if desired, the set also comprises a transactivation construct. This is desirable when the disease marker protein does not contain its own transactivation domain. The weapon, trigger, and transactivation constructs may also be provided individually, as can the fusion proteins they encode.

"Detectable markers" may be enzymes which catalyze reactions which produce a readily detectable product, typically a product with a color. Detectable markers may also provide to the host cell a readily observable phenotype, such as morphology, growth habit, or drug resistance. Toxic proteins can also be produced by the weapon construct, for example, cytotoxins such as ricin. Alternatively, the protein produced by the weapon construct may be an enzyme which metabolizes a pro-drug, converting it to a drug which is cytotoxic or cytostatic.

Methods for introduction of the genetic constructs of the present invention into cells are those which are available in the art. These include, but are not limited to transfection with naked or encapsulated nucleic acids, cellular fusion, protoplast fusion, and viral infection. Introduction of genetic constructs may be conducted in vitro or in vivo. Cells containing the constructs can be re-introduced to a body, for example by infusion or inoculation. Such methods can be used in the conventional manner.

Methods for detecting expression of the desired protein encoded on the weapon construct are any that are standardly used in the art for detection of marker proteins. Detection of particular enzymes or proteins expressed by the weapon construct may be by assay, by formation of colored product, observation of cellular or colony morphology, immunodetection methods, etc., as is convenient in a particular context for a desired protein. Such methods are well known in the art.

The following examples are provided for exemplification purposes only and are not intended to limit the scope of the invention which has been described in broad terms above.

EXAMPLES

Example 1

This example illustrates the general form of our strategy, using as the particular example of the gene on the "weapon" one which encodes a toxic product. The scheme is graphically depicted in FIG. 1.

Exogenous genes encoding "weapons" and "triggers" are delivered into cells. The "weapon" is encoded by a foreign, toxic gene whose expression is under the control of an inducible UAS (upstream activating sequence). The gene will not be expressed unless a functional, UAS-binding transcription factor is present in the cell. The "trigger" is encoded by a crippled transcription factor which can bind to the UAS through its DNA-binding domain (DBD) but cannot activate transcription because its transactivation domain (TAD) has been replaced with an amino acid sequence, the killer binding domain (KBD) that interacts with the target oncoprotein. In cells expressing adequate levels of the oncoprotein (termed the "killer"), a protein complex forms that can both bind to the UAS and activate transcription of the enzyme through a recruited TAD. The TAD can either be naturally present within the oncoprotein or, if the oncoprotein lacks a TAD, within another exogenously introduced protein that independently binds to the oncoprotein (see FIG. 1). The weapon will be expressed at high levels only in cells expressing high levels of the killer, resulting in cell death.

Example 2

This example demonstrates a test system used to validate the proposed strategy.

We made the following choices (FIG. 2). For the killer, we chose the p53 gene, which has been shown to be genetically altered in numerous tumor types (Hollstein, 1991). Immunohistochemical studies have shown that the resultant mutant p53 proteins are expressed at high levels in tumor cells but p53 is undetectable in most normal cells (Bartek, 1991). The p53 protein also contains a strong TAD at its amino-terminus (Fields, 1990; Raycroft, 1990). This TAD is preserved, though other properties of p53 are disrupted, in most p53 mutants (Zambetti, 1993). For the trigger, we chose protein domains known to bind to the carboxyl-terminus of p53, either from p53 itself (Iwabuchi, 1993; Milner, 1991; Jeffrey, 1995) or from the large T antigen of SV40 (Linzer, 1979; Ruppert, 1993). These domains were fused in frame to the DBD of GAL4. For the weapon, we chose the *E. coli* gene encoding polynucleotide phosphorylase (PNP), which can convert the non-toxic pro-drug 6-methylpurine deoxyribose (MeP-dR) to the diffusible, toxic 6-methylpurine (MeP) (Sorscher, 1994). The PNP gene was placed under the control of a GAL4 responsive promoter, $UAS_G$.

Plasmid Construction. "Trigger" plasmids contained the DNA-binding domain (DBD) of GAL4 (aa 1–147; Sadowski, 1989) fused in frame to a protein domain that could bind p53 (p53BD). In trigger TA, the p53BD consisted of amino acids (aa) 84–708 of the SV40 large T antigen (from pTD1, Clontech, Palo Alto, Calif.), separated from the DBD by the 7 aa spacer PEFGLRP. In trigger P5, the p53BD consisted of aa 305–393 of human p53 (from pCEP4-p53WT, (Pietenpol, 1994), separated from the DBD by the 5 aa spacer PEFPG. In both cases, the p53BD domains were inserted into a vector derived from pSGVP(Finkel, 1993) containing the GAL4 DBD. The "weapon" plasmid contained the bacterial DeoD gene, coding for PNP(Hershfield, 1991), amplified from *Escherichia coli* genomic DNA and modified to contain a consensus eukaryotic translation start sequence (Kozak, 1992). The DeoD gene was placed under control of a GAL4-responsive promoter obtained from pG5E1b-CAT (Finkel, 1993) to create $UAS_G$-PNP. The GAL4-responsive $UAS_G$ -βgal construct was identical to $UAS_G$-PNP except that the DeoD gene was replaced with the β-galactosidase gene from pCMV-β-gal (Clontech). The "killer" plasmids were pCEP4-p53 (WT or mutants R175H, R248W, or R273H), each containing the complete p53 coding sequence under control of the CMV promoter (Pietenpol, 1994). The construction of these plasmids was generally performed by PCR amplification of the indicated templates.

Example 3

This example demonstrates the testing of the trigger construct.

Figure 3A:
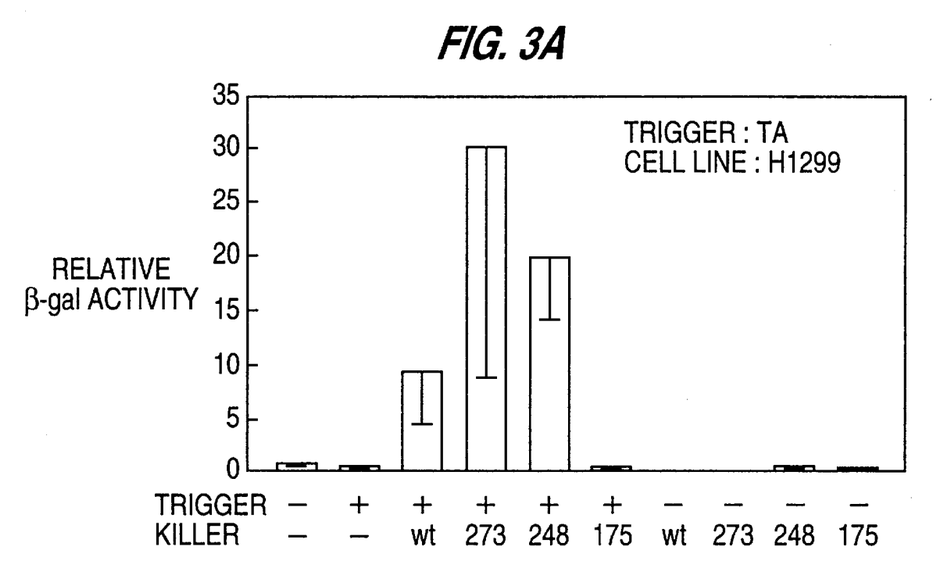
Figure 3B:
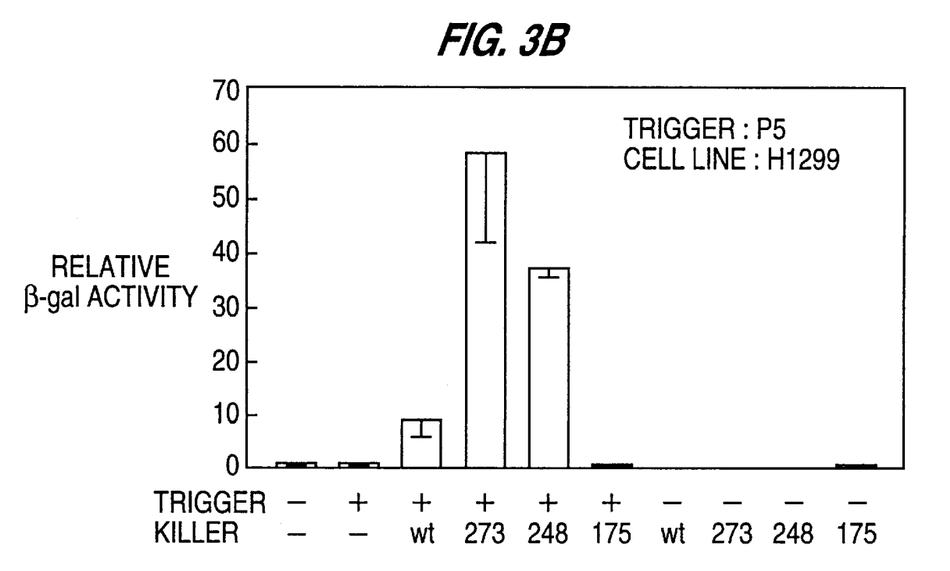
Figure 3C:
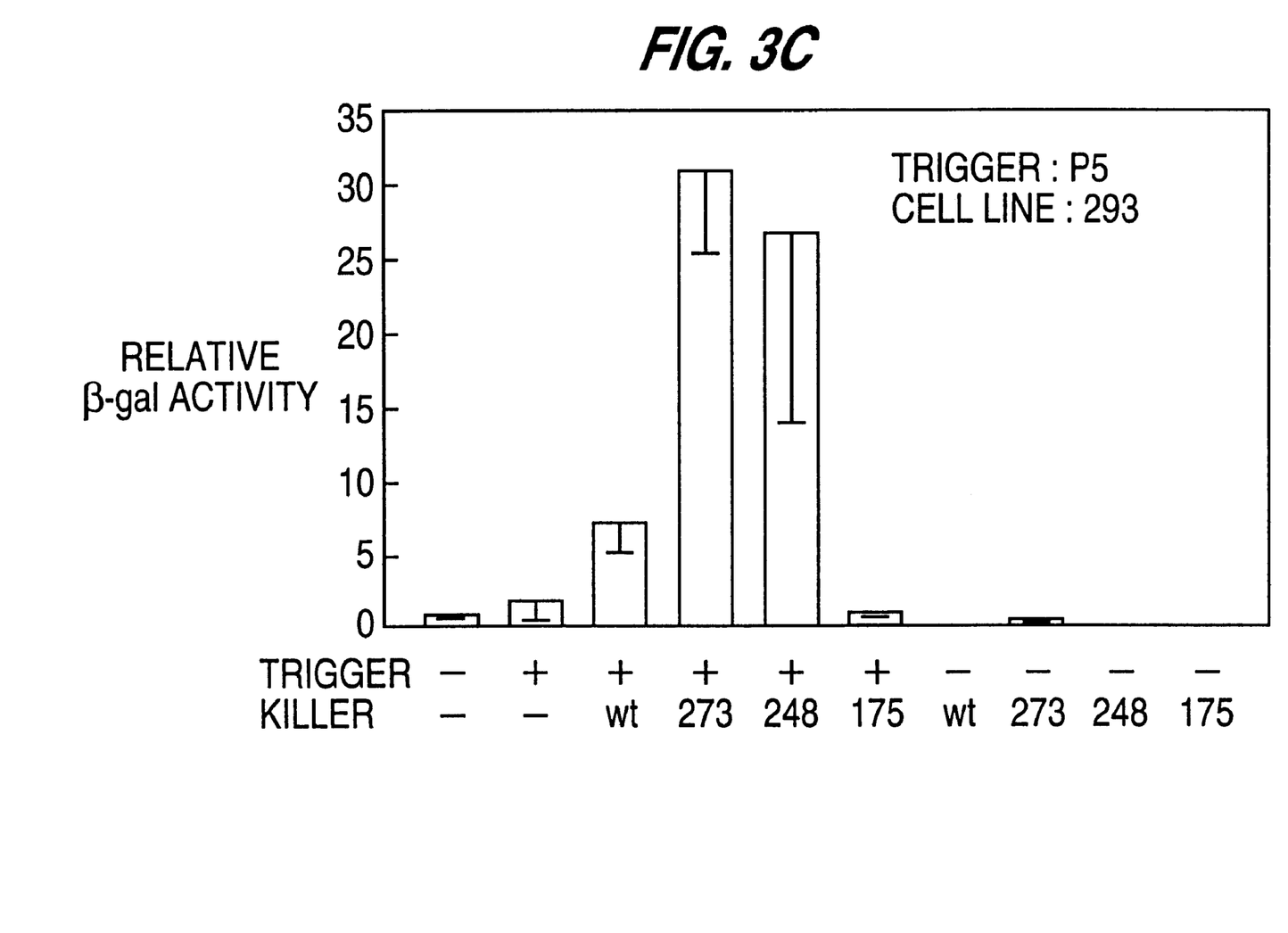

Each of the components illustrated in FIGS. 1 and 2 can be independently optimized. We first tested the ability of various triggers to stimulate transcription of a $UAS_G$-controlled reporter gene in a p53-dependent manner. Two different human cell lines were used. The p53-null H1299 cell line was derived from a lung cancer (Chen, 1993) and the 293 line was derived from human embryonic kidney cells transformed with adenovirus DNA (Graham, 1977). The TAD of the endogenous p53 in 293 cells is inactivated by the adenovirus encoded E1B protein (Yew, 1994). The 293 cells are more efficient recipients for PEI-mediated gene transfer than H1299 cells. Several trigger constructs were evaluated in these lines, and the most efficient chosen for further experiments (FIG. 2B). When H1299 cells were transfected with the TA trigger plus a $UAS_G$-controlled β-galactosidase (β-gal) reporter, only very low levels of β-gal activity could be detected (FIG. 3). However, when p53 was overexpressed in these cells as a result of p53 gene transfer, β-gal levels were increased by up to 30-fold. Three of the most common p53 mutants were tested in these assays. The R248W and R273H mutants were effective, while the R175H mutant was not. These results were consistent with the defective transactivation properties of the latter (Fields, 1990; Raycroft, 1990). As expected, the wt p53 protein also showed activity in this system, though less than the R248W and R273H mutants, probably because of the greater protein stability of mutant forms of p53 (Zambetti, 1993). The P5 trigger also proved effective at conferring a p53-dependent expression of the reporter, in both H1299 and 293 cells. The results with P5 confirm those of Oren and co-workers, demonstrating the ability of the C-terminus of p53 to bind intact p53 and recruit its transactivation domain (Shaulian, 1993).

Cell Culture and Transfections. The 293 cell line (Graham, 1977) was obtained from ATCC and cultured in DMEM medium (Life Technologies, Gaithersburg, Md.) supplemented with 10% fetal bovine serum and antibiotics (FBSA). H1299 cells were obtained from A. Fornace (Chen, 1993) and grown in Ham's F-12 medium (Life Technologies) with FBSA. For transfections, cells were plated at a density of 5–8×10⁴ cells per well of a 24-well tissue culture plate. Transfections were performed 36–60 h after plating, when cells were almost confluent, essentially as described in(Boussif, 1995). Briefly, cells were washed once with OPTIMEM (Life Technologies) and 400 µl of OPTIMEM were added to each well. Two µg of each plasmid in 3 mM Tris, 0.2 mM EDTA were mixed with a sufficient amount of pBluescript (Stratagene, La Jolla, Calif.) and NaCl (150 mM) to constitute 6 µg plasmid DNA in a total volume of 50 µl. A mixture of 12 µl polyethylenimine (PEI, 0.9 mg/ml) and 38 µl NaCl (150 mM) was then added to the DNA. After a 10–30 min incubation at room temperature, the DNA-PEI mix was added to each well. Two to four hours later, the liquid in the wells was aspirated and replaced with culture medium.

β-Gal Assays. Cells used for β-gal assays were harvested 24–48 hours after transfection. Cells were washed once with Hank's balanced saline solution (HBSS) and subjected to three cycles of freezing and thawing in 100 µl of phosphate buffered saline (PBS). Cell lysates were transferred to microfuge tubes containing 11µ of 10 mM dithiothreitol (DTT) in PBS, pelleted for 10 min at 4° C. and stored at -20° C. until assayed for β-gal activity. In a typical assay, 50 µl of cell lysate were added to 450 µl of reaction buffer (60 mM $Na_2HPO_4$, 40 mM $NaH_2PO_4$, 10 mM KCl, 1 mM $MgSO$, pH 7.0, 0.27% β-mercaptoethanol). Following a 5 min pre-incubation at 28° C., reactions were initiated by addition of 100 µl of a 4 mg/ml solution of ortho-nitrophenyl-galactoside (ONPG) in reaction buffer (Kern, 1992). Reactions were stopped by addition of 250 µl of 1M $Na_2CO_3$ and absorbances at 420 nm measured.

Example 4

This example demonstrates that the observed cytotoxicity in the system is dependent on the presence of the oncogene p53.

Figure 4A:
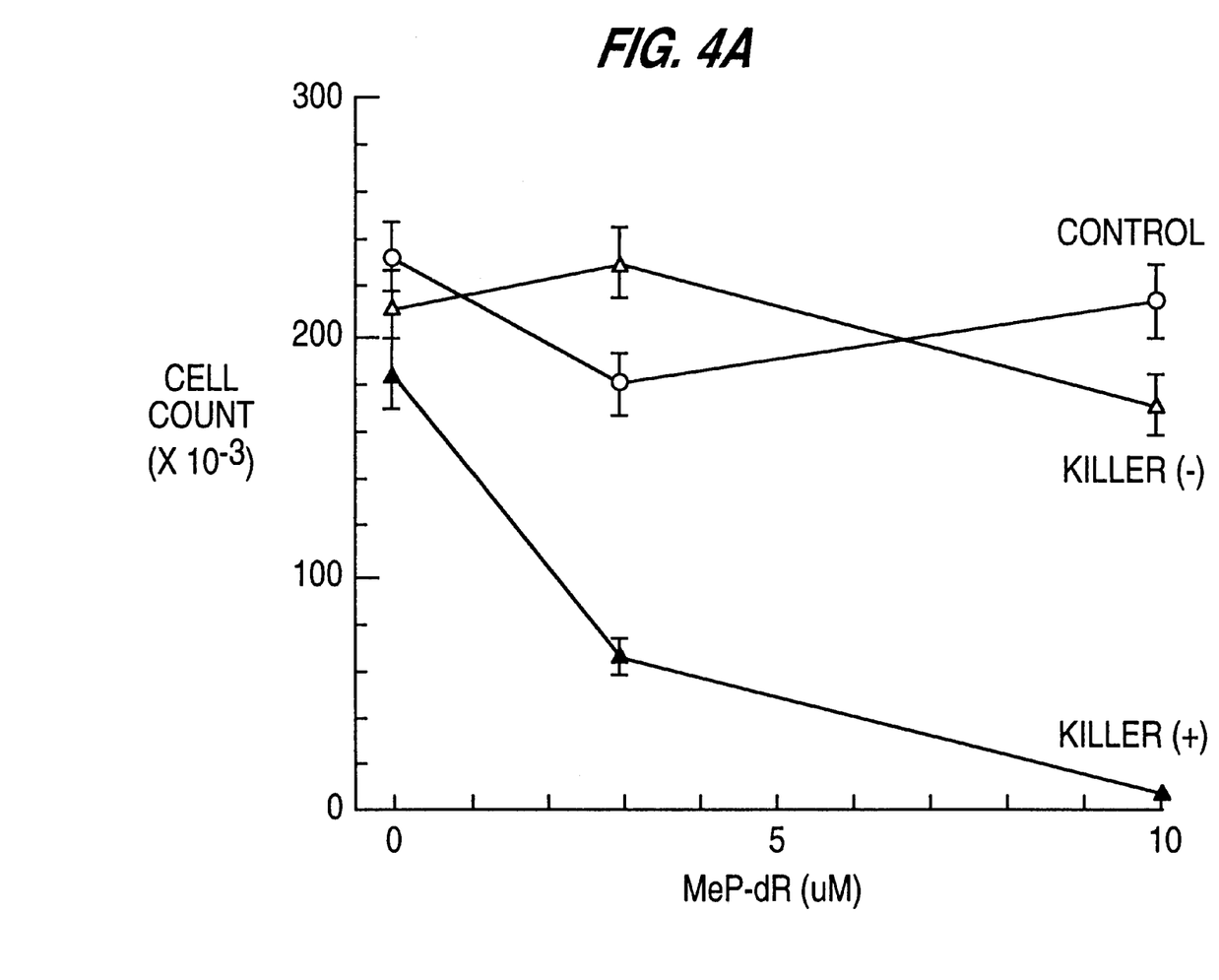
Figure 4B:
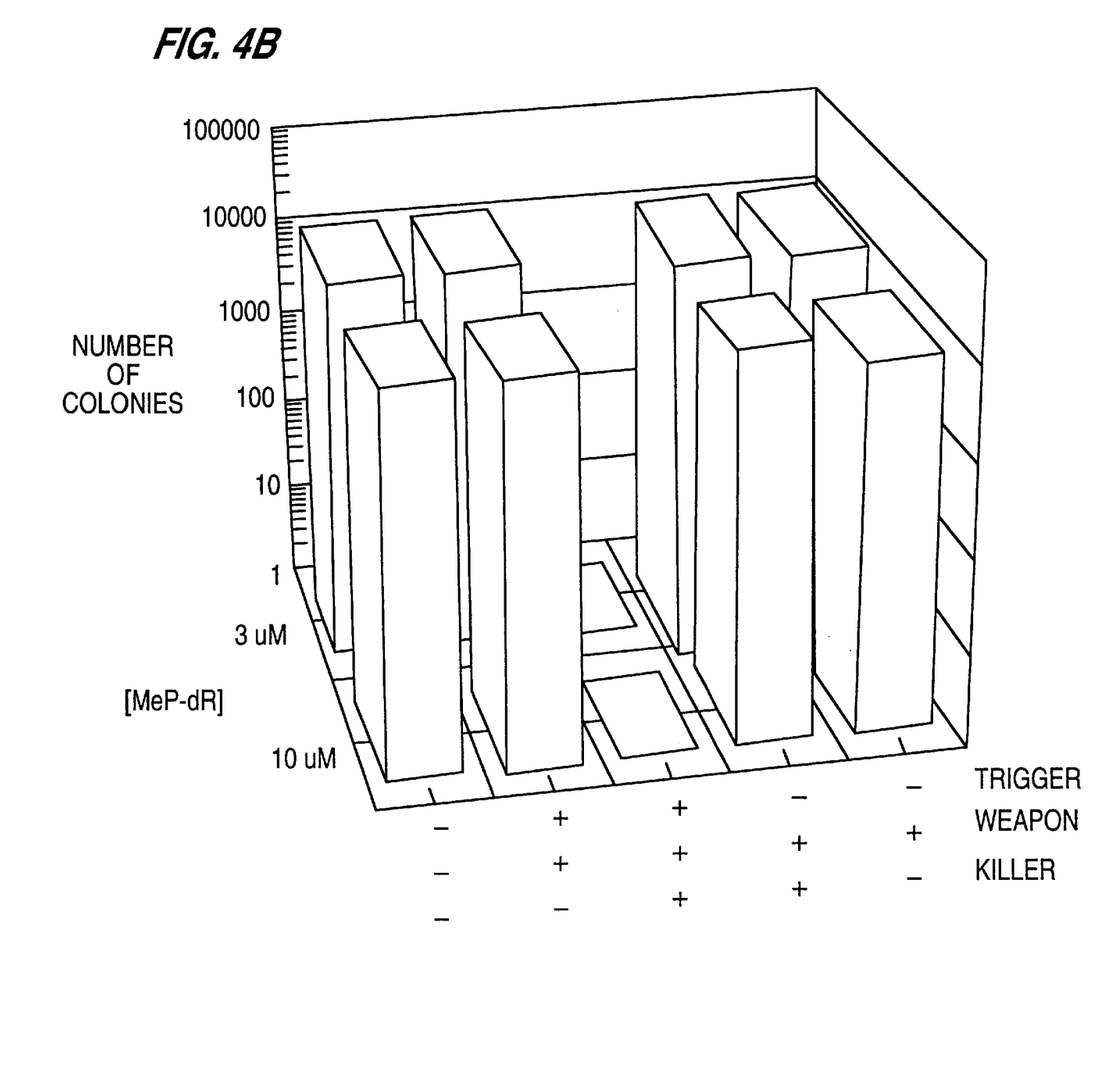
Figure 5:
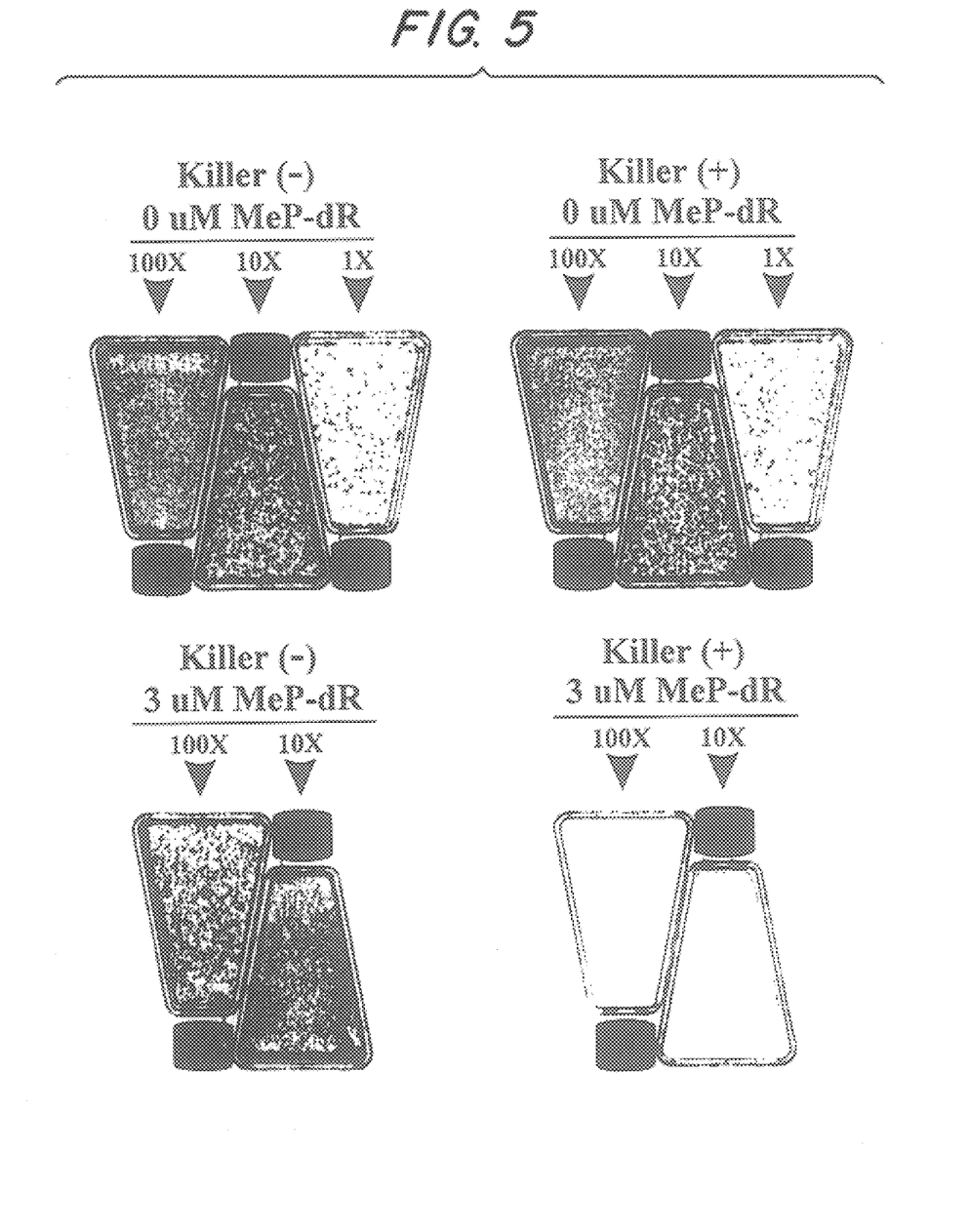
FIG. 5 provides representative examples of colony-forming assays after drug treatment. H1299 cells were transfected with weapon and trigger constructs, with or without killer (p53R273H), as indicated. Five days following treatment with MeP-dR, the cells were harvested and seeded into new 25 cm$^2$ flasks. Sixty-seven percent, 6.7%, and 0.67% of the cells from each transfected well were seeded in the flasks marked 100×, 10×, and 1×, respectively. Eight days later, the colonies were stained with crystal violet and photographed.

We sought to determine whether this p53-induced expression of a $UAS_G$-controlled gene could be translated into differential killing of p53-overexpressing cells. We chose H1299 cells for these experiments, as the absence of all endogenous p53 in this line simplified interpretation. H1299 cells were transfected with both a trigger (P5) and a weapon ($UAS_G$-PNP), with or without a killer (p53-R273H). Various amounts of MeP-dR were added to the culture medium one day after transfection and cell number and viability assessed five days later. A dramatic difference in MeP-dR sensitivity was observed between cells transfected with or without the killer (FIGS. 4 and 5). At drug concentrations of 3–10 µM, most cells without p53 remained healthy and continued to proliferate. In contrast, after co-transfection with the killer, only a relatively small number of cells remained (FIG. 4A). Cells transfected with the killer and weapon, but without the trigger, also remained healthy. These and additional controls (see below) demonstrated that only the combination of weapon, trigger, and killer resulted in substantial cell death at low drug concentrations.

Cellular Viability Assays. One day after transfection, MeP-dR was added to the culture medium to final concentrations of 0, 3, or 10 µM. Five days later, cells were harvested by trypsinization and suspended in a final volume of 600 µl. A 50 µl aliquot of cells was mixed with an equal volume of 1% NP40, 6.7% formaldehyde, 20 µg/ml Hoechst 33258 in PBS for counting and assessing nuclear morphology. Over 90% of cells with a normal nuclear morphology were found to exclude dye (Wotring, 1985) in control experiments. For colony-forming assays, aliquots of 400, 40, or 4 µl were plated in 25 cm² tissue culture flasks in 5 ml of the appropriate medium. After 6–8 days, colonies were stained with crystal violet and counted.

Example 5

This example demonstrates that colony forming ability is another useful assay for drug toxicity.

In these experiments and others, we noted that the number of morphologically intact cells was an inadequate measure of drug toxicity. When cells were harvested and replated after drug treatment, many of the apparently intact, dye-excluding cells proved incapable of growing (compare FIGS. 4A and B at 3 µM MeP-dR). Accordingly, there was a striking difference in colony-forming ability between cells expressing killer, trigger, and weapon versus those expressing only trigger and weapon following exposure to drug. Representative examples of the colonies formed after MeP-dR treatment of such cells are shown in FIG. 5 and the results quantitated in FIG. 4B. At 3 or 10 µM MeP-dR, there was over a 1000-fold greater effect in the p53-expressing cells compared to the cells without p53. It is also important to note that the PEI protocol transduced less than 3% of the H1299 cells, as assessed by β-gal staining. The fact that virtually all H1299 cells were incapable of forming colonies following appropriate transfection and MeP-dR treatment attests to the powerful bystander effect of this system.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES

1. Stillman, B. (1994) 59*th Cold Spring Harbor symposium on Quantitative Biology—The Molecular Genetics of Cancer* (Cold Spring Harbor Lab. Cold Spring Harbor).
2. Karp, J. E. & Broder, S. (1995) *Nature Medicine* 1, 309–320.
3. Sadowski, I. & Ptashne, M. (1989) *Nucleic Acids Res* 17, 7539.
4. Pietenpol, J. A., Tokino, T., Thiagalingam, S., el-Deiry, W. S., Kinzler, K. W. & Vogelstein, B. (1994) *Proc Natl Acad Sci USA* 91, 1998–2002.
5. Fearon, E. R., Finkel, T., Gillison, M. L., Kennedy, S. P., Casella, J. F., Tomaselli, G. F., Morrow, J. S., & Van Dang, C. *Proc Natl Acad Sci USA* 89, 7958–62.
6. Hershfield, M. S., Chaffee, S., Koro-Johnson, L., Mary, A., Smith, A. A. & Short, S. A. (1991) *Proc Natl Acad Sci USA* 88, 7185–9.
7. Kozak, M. (1992) *Annu Rev Cell Biol* 8, 197–225.
8. Graham, F. L., Smiley, J., Russell, W. C. & Nairn, R. (1977) *J Gen Virol* 36, 59–74.
9. Chen, J. Y., Funk, W. D., Wright, W. E., Shay, J. W. & Minna, J. D. (1993) *Oncogene* 8, 2159–66.
10. Boussif, O., Lezoualc'h, F., Zanta, M. A., Mergny, M. D., Scherman, D. l, Demeneix, B. & Behr, J. P. (1995) *Proc Natl Acad Sci USA* 92, 7297–301.
11. Kern, S. E., Pietenpol, J. A., Thiagalingam, S., Seymour, A., Kinzler, K. W., & Vogelstein, B. (1992) *Science* 256, 827–30.
12. Wotring, L. L., Passiatore, J. E., Roti Roti, J. L., Hudson, J. L. & Townsend, L. B. (1985) *Cancer Res* 45, 6355–61.

13. Keegan, L., Gill, G. & Ptashne, M. (1986) *Science* 231, 699–704.
14. Fields, S. & Sternglanz, R. (1994) *Trends Genet* 10, 286–92.
15. Gyuris, J., Golemis, E., Chertkov, H. & Brent, R. (1993) *Cell* 75, 791–803.
16. Moolten, F. L. & Wells, J. M. (1990) *J Natl Cancer Inst* 82, 297–300.
17. Blaese, R. M., Ishii-Morita, H., Mullen, C., Ramsey, J., Ram, Z., Oldfield, E. & Culver, K. (1994) *Eur J Cancer* 30A, 1190–3.
18. Sorscher, E. J., Peng. S., Bebok, Z., Allan, P. W., Bennett, L. L. J., and Parker W. B. (1994) *Gene Therapy* 1, 233–238.
19. Huber, B. E. Richards, C. A., & Austin, E. A. (1994) *Ann N Y Acad Sci* 716, 104–14.
20. Hollstein, M., Sidransky, D., Vogelstein, B. & Harris, C. C. (1991) *Science* 253, 49–53.
21. Bartek, J., Bartkova, J., Vojtesek, B., Staskova, Z., Lukas, J., Rejthar, A., Kovarik, J., Midgley, C. A., Gannon, J. V. & Lane, D. P. (1991) *Oncogene* 6, 1699–703.
22. Fields, S. & Jang, S. K. (1990) *Science* 249, 1046–9.
23. Raycroft, L., Wu, H. Y. & Lozano, G. (1990) *Science* 249, 1049–51.
24. Zambetti, G. P. & Levine, A. J. (1993) *Faseb J* 7, 855–65.
25. Iwabuchi, K., Li, B., Bartel, P. & Fields, S. (1993) *Oncogene* 8, 1693–6.
26. Milner, J., Medcalf, E. A. & Cook, A. C. (1991) *Mol Cell Biol* 11, 12–9.
27. Jeffrey, P. D., Gorina, S. & Pavletich, N. P. (1995) *Science* 267, 1498–502.
28. Linzer, D. I. & Levine, A. J. (1979) *Cell* 17, 43–52.
29. Ruppert, J. M. & Stillman, B. (1993) *Mol Cell Biol* 13, 3811–20.
30. Yew, P. R., Liu, X. & Berk, A. J. (1994) *Genes Dev* 8, 190–202.
31. Cho, Y., Gorina, S., Jeffrey, P. D. & Pavletich, N. P. (1994) *Science* 265, 346–55.
32. Baker, S. J., Markowitz, S., Fearon, E. R., Willson, J. K. & Vogelstein, B. (1990) *Science* 249, 912–5.
33. Shaulian, E., Zauberman, A., Milner, J., Davies, E. A. & Oren, M. (1993) *Embo j* 12, 2789–97.
34. Germino, F. J., Wang, Z. X. & Weissman, S. M. (1993) *Proc Natl Acad Sci USA* 90, 933–7.
35. Oren, M. (1994) *Semin Cancer Biol* 5, 221–7.
36. Ram, Z., Walbridge, S., Shawker, T., Culver, K. W., Blaese, R. M. & Oldfield, E. H. (1994) *J Neurosurg* 81, 256–60.
37. Chen, S. H., Chen, X. H., Wang, Y., Kosai, K., Finegold, M. J., Rich, S. S. & Woo, S. L. (1995) *Proc Natl Acad Sci USA* 92, 2577–81.
38. Clayman, G. L., el-Naggar, A. K., Roth, J. A., Zhang, W. W., Goepfert, H., Taylor, D. L. & Liu, T. J. (1995) *Cancer Res* 55, 1–6.
39. Hurford, R. K., Jr., Dranoff, G., Mulligan, R. C. & Tepper, R. I. (1995) *Nat Genet* 10, 430–5.
40. Smythe, W. R., Hwang, H. C., Elshami, A. A., Main, K. M., Eck, S. L., Davidson, B. L., Wilson, J. M., Kaiser, L. R. & Albelda, S. M. (1995) *Ann Surg* 222, 78–86.
41. Jain, R. K. (1994) *Sci Am* 271, 58–65.

We claim:

1. A set of genetic constructs comprising (1) a weapon construct, and (2) a trigger construct, wherein:

the weapon construct comprises (a) a gene coding sequence of a desired protein, and (b) an inducible upstream activating sequence which is upstream of the gene coding sequence, wherein the gene coding sequence is inducible by a transcription factor which binds to the upstream activating sequence; and the trigger construct comprises a nucleotide sequence encoding a first fusion protein comprising (c) a DNA-binding domain which can bind to the upstream activating sequence, and (d) a killer binding domain which binds to a disease marker protein which is selectively expressed in a diseased cell, wherein the first fusion protein does not contain a transactivation domain.

2. The set of genetic constructs of claim 1 further comprising (3) a transactivation construct which comprises a nucleotide sequence encoding a second fusion protein comprising (e) a killer binding domain which binds to the disease marker protein, and (f) a transactivation domain which when part of a protein complex which binds to the upstream activating sequence activates expression of the weapon construct.

3. The set of claim 1 wherein the desired protein is a detectable marker.

4. The set of claim 1 wherein the desired protein is toxic to a cell.

5. The set of claim 1 wherein the desired protein converts a pro-drug to a drug which is toxic to a cell.

* * * * *